United States Patent [19]

Boswell et al.

[11] Patent Number: 4,990,617
[45] Date of Patent: Feb. 5, 1991

[54] N-OXIDE PRODRUG DERIVATIVES OF 3-HYDROXY MORPHINANS AND PARTIAL MORPHINANS AND DERIVATIVES

[75] Inventors: George A. Boswell; Melvyn J. Myers, both of Wilmington, Del.

[73] Assignee: E. I. Du Pont de Nemours and Company, Wilmington, Del.

[21] Appl. No.: 391,406

[22] Filed: Jul. 27, 1989

Related U.S. Application Data

[60] Continuation of Ser. No. 103,213, Oct. 1, 1987, abandoned, which is a division of Ser. No. 803,222, Dec. 2, 1985, Pat. No. 4,722,928.

[51] Int. Cl.$^5$ .................. C07D 221/26; C07D 221/28; C07D 487/08
[52] U.S. Cl. ........................................ 546/44; 546/46; 540/477
[58] Field of Search .................... 546/44, 46; 540/477; 514/282

[56] References Cited

U.S. PATENT DOCUMENTS

| | | | |
|---|---|---|---|
| 2,813,097 | 11/1957 | Tiffany | 546/74 |
| 2,813,098 | 11/1957 | Tiffany | 546/74 |
| 3,131,185 | 1/1964 | Lafon | 546/74 |
| 3,144,459 | 8/1964 | Sawa et al. | 546/43 |
| 3,217,006 | 11/1965 | Sawa et al. | 546/74 |
| 3,299,072 | 1/1967 | Bartels-Keith | 546/44 |
| 4,722,928 | 2/1988 | Boswell et al. | 514/282 |

OTHER PUBLICATIONS

K. Orzechowska, *Arch. Immunol. Ther. Exp.* 15 (2), 290 (1967).
B. Bobranski and J. Pomorski, *Arch. Immunol. Ther. Exp.* 14 (1), 121 (1966).
M. Polonovski et al., *Bull Acad. Med.* 103, 174 (1930).
N. H. Chang et al., *J. Org. Chem.* 15, 634 (1950).
B. Kelentei et al., *Arzneimittel-Forsch* 7, 594 (1957).
K. Takagi et al., *Yakugaku* 83, 381 (1963) (*Chem. Abs.* 59; 9224 b).
M. R. Fenessy, *Brit. J. Pharmacol.* 34, 337 (1968).
M. R. Fennessy, *Eur. J. Pharmacol.* 8, 261 (1969).
M. R. Fennessy, *J. Pharm. Pharmacol.* 21, 668 (1969).
J. D. Phillipson et al., *Eur J. Drug Metabl. Pharmacokinetics* 3, 119 (1978).
T. Ishida et al., *Drug Metab. Dispos.* 7, 1962 (1979).
T. Ishida et al., *J. Pharmacobio-Dyn.* 5, 521 (1982).
S. Y. Yeh et al., *J. Pharma. Sci.* 68, 133 (1979).
R. L. Heimans et al., *J. Pharm. Pharmacol.* 23, 831 (1971).
T. Chyczewski, *Pol. J. Pharmacol. Pharm.* 25, 373 (1973).
P. Jenner et al., *Xenobiotica* 3 (6) 341 (1973).
Burger, Medicinal Chemistry, Third Edition, Part 1, pp. 50–53 Wiley-Interscience (1971).
The Merck Index, Tenth Edition, pp. 207, 213, 911, 912, 999, 1024 Pub. by Merck and Co., Inc. (1983).
Klingsberg, "Pyridine and its Derivatives" Part Two, pp. 97–112, 114 Interscience Pub. 1961.
Burger, Medicinal Chemistry, Third Edition, Part I, pp. 50–53, Wiley—Interscience (1970).

*Primary Examiner*—Alan L. Rotman

[57] ABSTRACT

N-oxide prodrug derivatives of 3-hydroxy morphinan and partial morphinan analgesics, agonist-antogonists, and narcotic antagonists are useful therapeutic entities which provide enhanced bioavailability of 3-hydroxy morphinans and partial morphinans from orally administered dosage forms.

2 Claims, No Drawings

[4,990,617]

N-OXIDE PRODRUG DERIVATIVES OF 3-HYDROXY MORPHINANS AND PARTIAL MORPHINANS AND DERIVATIVES

This application is a continuation of application Ser. No. 07/103,213 filed Oct. 1, 1987 (abandoned) which is a division of application Ser. No. 06/803,222, filed Dec. 2, 1985, now U.S. Pat. No. 4,722,928.

BACKGROUND OF THE INVENTION

1. Field of Invention

This invention relates to N-oxide prodrug derivatives of 3-hydroxy morphinan and partial morphinan analgesics, agonist-antagonists, and narcotic antagonists having improved oral bioavailability, as well as pharmaceutical compositions comprising these compounds and suitable pharmaceutical carriers, methods of treating pain of reversing the effects of narcotic drugs such as morphine in a mammal using the prodrugs, and methods for preparing the prodrugs.

2. Background Art

The psychological and other medicinal properties of opium have been known since ancient times. It was not until the beginning of the nineteenth century, however, that morphine was isolated from opium. Codeine and papaverine were isolated not long thereafter, and by the middle of the nineteenth century, use of the pure alkaloids rather than crude opium preparations was becoming established medical practice.

Morphine and codeine are by far the most important naturally occurring opium alkaloids. They share the phenanthrene or morphinan ring structure. Since the morphine structure was elucidated in the early part of this century, a host of semisynthetic and synthetic derivatives have been prepared. A major focus of this research has been to find strong analgesic compounds without the abuse potential, physical-dependence and tolerance-producing characteristics that limit the usefulness of the opium alkaloids.

Another important goal in preparing derivatives of morphine has been to find potent analgesic compounds with improved oral efficacy. Due to significant first-pass metabolism in the liver and intestinal wall, many 3-hydroxy morphinans are significantly less effective orally than parenterally. For this reason, many 3-hydroxy morphinans, including morphine and buprenorphine, are administered mainly by injection. Codeine, on the other hand, has a much higher oral:parenteral potency ratio than morphine. Structurally, codeine is simply 3-methyl-morphine. The action of morphine is terminated largely by glucuronide conjugation at the 3-hydroxyl group, and the 3-methoxy group is believed to protect codeine from rapid first-pass biotransformation. Oxycodone, which also has a 3-methoxy group, has similarly good oral potency.

Many of the semisynthetic morphinan derivatives which have been prepared involve only small modifications of easily changed peripheral groups, e.g., hydromorphone, oxymorphone, oxycodone, and hydrocodone. All are narcotic analgesics like morphine and codeine, and all exhibit some measure of addiction liability.

A number of compounds possessing only a portion of the morphine ring nucleus have also been prepared. Archer, Belg. Patent No. 611,000, discloses 2-dimethallyl-5,9-dimethyl-2'-hydroxybenzomorphan, commonly called pentazocine. Meperidine, 1-methyl-4-phenyl-4-piperidine-carboxylic acid ethyl ester, and methadone, 6-(dimethylamino)-4,4-diphenyl-3-heptanone, are wholly synthetic compounds having little structural similarity to morphine. Like morphine, these compounds have analgesic properties. Unfortunately, they also have addiction potential.

Several morphinan derivatives having various substituents on the nitrogen atom have been found to exhibit narcotic antagonist as well as narcotic analgesic activity. Such compounds are referred to as agonist-antagonists. Pachter and Matossian, U.S. Pat. No. 3,393,197, disclose N-substituted-14-hydroxydihydronormorphines, including the N-cyclobutylmethyl derivative, commonly called nalbuphine. Monkovik and Thomas, U.S. Pat. No. 3,775,414, disclose N-cyclobutylmethyl-3,14-dihydroxymorphinan, commonly called butorphanol. Bentley et al., U.S. Pat. No. 3,433,791, disclose 17-(cyclopropylmethyl)-α-(1,1-dimethylethyl)-4,5-epoxy-18,19-dihydro-3-hydroxy-6-methoxy-α-methyl-6,14-ethenomorphinan-7-methanol, commonly called buprenorphine.

Still other N-substituted morphinan derivatives are pure narcotic antagonists with little or no agonist activity. Lewenstein, U.S. Pat. No. 3,254,088, discloses N-allyl-7,8-dihydro-14-hydroxynormorphinone, commonly known as naloxone. Pachter and Matossian, U.S. Pat. No. 3,332,950, disclose N-substituted-14-hydroxydihydro-normorphinones including the N-cyclopropylmethyl analog, commonly known as naltrexone. Compounds of these two patents are narcotic antagonists.

The definition of narcotic antagonism adopted in the present invention is that of Archer and Harris, in their chapter on this topic in *Progress in Drug Research*, Vol. 8, 1965, pages 261 to 320, wherein narcotic antagonists are defined as compounds which "have the remarkable property of reversing the major pharmacodynamic actions of the narcotics . . . Strictly speaking we consider a substance to be a narcotic antagonist if it can reverse the more prominent effects of morphine such as analgesia, sedation, respiratory depression, and myosis."

The N-oxides of certain morphinan derivatives are also known in the prior art, e.g., Tiffany, U.S. Pat. No. 2,813,097, discloses 3-hydroxy-N-methylmorphinan N-oxide and its utility as an analgesic. Tiffany, U.S. Pat. No. 2,813,098, discloses 3-methoxy-N-methylmorphinan N-oxide and its utility as an antitussive. Although it is stated that these N-oxides have a higher therapeutic index than the corresponding tertiary amines, there is no suggestion that the N-oxide of 3-hydroxy-N-methyl morphinan might have improved oral bioavailability relative to the parent compound.

Bartels-Keith, U.S. Pat. No. 3,299,072, discloses thebaine derivatives of the formula

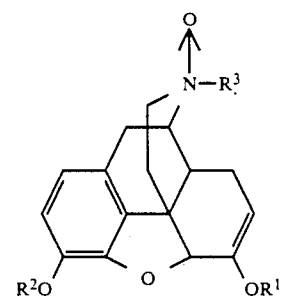

in which $R^1$ is $C_1$–$C_4$ alkyl, $R^2$ is $C_1$–$C_4$ alkyl, hydrogen, or an acyl residue from a carboxylic acid having up to 8 carbon atoms, and R is an unsaturated alkyl group or a cycloalkyl group having up to 8 carbons. These compounds have analgesic an/or narcotic antagonist activity. The reference claims the tertiary amines, the N-oxides, and various salts of the stated formula without distinguishing the N-oxides in any way. There is no mention of route of administration.

Sawa, Maeda, and Tsuji, U.S. Pat. Nos. 3,144,459 and 3,217,006, disclose the compound of the formula

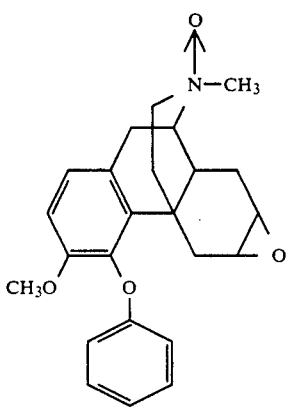

as a synthetic intermediate to 3-methoxy-4-phenoxy N-methyl-morphinan.

N-oxide derivatives of other non-morphinan analgesics have been reported. W. Graf, Swiss Patent No. 481,124, discloses the compound of the formula

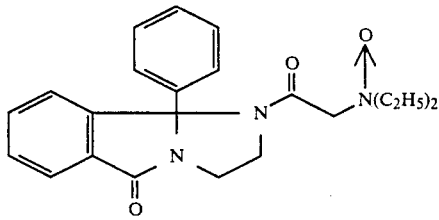

This compound possesses analgesic, sedative, antitussive, hypotensive, and spasmolytic properties.

K. Orzechowsak, *Arch. Immunol. Ther. Exp.* 15(2), 290 (1967), and B. Bobranski and J. Pomorski, *Arch. Immunol. Ther. Exp.* 14(1), 121 (1966) report the preparation of the N-oxides of certain 1-alkyl-4-phenyl-4-acyloxy piperidine compounds. The N-oxide of 1-methyl-4-phenyl-4-propionoxypiperidine HCl exhibited analgesic activity equal to that of dolantin HCl, but of longer duration. Toxicity was also less.

The N-oxides of morphine and simple morphine derivatives such as codeine, hydromorphone (dihydromorphinone), and hydrocodone (dihydro codeinone), are well known, having been reported by, among others: M. Plonovski et al, *Bull. Acad. Med.* 103, 174 (1930); N. H. Chang et al, *J. Org. Chem.* 15, 634 (1950); B. Kelentei et al, *Arzneimittel-Forsch.* 7, 594 (1957); K. Takagi et al, *Yakugaku Zasshi* 83, 381 (1963) (*Chem. Abs.* 59:9224b); L. Lafon, U.S. Pat. No. 3,131,185; M. R. Fennessy, *Brit. J. Pharmacol.* 34, 337 (1968); M. R. Fennessy, *Eur. J. Pharmacol.* 8, 261 (1969); and M. R. Fennessy, *J. Pharm. Pharmacol.* 21, 668 (1969). MOrphine N-oxide is variously reported to be either less active or inactive as an analgesic but an effective antitussive, as well as having somewhat lower toxicity than morphine. There is no indication, however, that these N-oxides were ever administered orally, nor any suggestion that they might exhibit improved oral bioavailability.

Woods, Brit. Patent No. 1,217,296, discloses the use of a combination of morphine N-oxide and amiphenazole as an analgesic composition. The combination is said to enhance the analgesic activity of morphine N-oxide while reducing the side effects of both compounds.

Oxidative metabolism to an N-oxide which is excreted is among the many metabolic pathways which have been identified in mammals administered various tertiary amines. J. D. Phillipson et al, *Eur. J. Drug Metab. Pharmacokinetics* 3, 119 (1978), report that morphine and codeine are converted in part to the corresponding N-oxides by a guinea pig liver microsomal preparation, and also that these two drugs are partially metabolized to the N-oxides when administered to rats. T. Ishida et al, *Drug Metab. Dispos.* 7, 162 (1979), and T. Ishida et al, *J. Pharmacobio-Dyn.* 5, 521 (1982), report that oxycodone N-oxide is one of a number of identifiable metabolites found in the urine of rabbits administered oxycodone subcutaneously. While other metabolites were found in both free and conjugated forms, oxycodone-N-oxide was found only in the free, unconjugated form. The analgesic activity of oxycodone is believed to be due to the unchanged drug rather than the metabolites. S. Y. Yeh et al, *J. Pharm. Sci.* 68, 133 (1979), also report isolating morphine N-oxide from the urine of guinea pigs administered morphine sulfate.

Certain tertiary amine N-oxides are partially metabolized by reduction to the tertiary amine upon administration to test animals. R. L. H. Heimans et al, *J. Pharm. Pharmacol.* 23, 831 (1971) report that morphine N-oxide is partially reduced to morphine after administration to rats. T. Chyczewski, *Pol. J. Pharmacol. Pharm.* 25, 373 (1973), reports that the N-oxide of 1-methyl-4-phenyl-4-piperidinol propionate is partially reduced to the tertiary amine following administration to rabbits, mice, and rats. P. Jenner et al, *Xenobiotica* 3 (6), 341 (1973), report that nicotine-1'--N-oxide is partially reduced to nicotine in man after oral administration, but not after intravenous administration. Oral administration of nicotine-1'-N-oxide substantially avoids the first-pass phenomenon seen with oral nicotine. The reduction to nicotine which occurs in the lower gastrointestinal tract is believed to be by GI flora.

The oral administration of many drugs will elicit a substantially lesser response as compared to an equal dose administered parenterally. This reductive in potency most commonly results from the extensive metabolism of the drug during its transit from the gastrointestinal tract to the general circulation. For example, the intestinal mucosa and the liver, through which an orally administered drug passes before it enters the systemic circulation, are very active enzymatically and can thus metabolize the drug in many ways.

When an orally administered drug is rapidly metabolized to an inactive or significantly less active form by the gastrointestinal system or liver prior to entering the general circulation, its bioavailability is low. In certain instances, this problem can be circumvented by administering the drug by another route. Examples of such alternative routes include nasal (propranolol), sublingual (nitro-glycerin) and inhalation (cromolyn sodium).

Drugs administered by these routes avoid hepatic and gut-wall metabolism on their way to the systemic circulation.

In some instances, the presystemic metabolism of certain orally administered drugs can be overcome by derivatization of the functional group in the molecule that is susceptible to gastrointestinal or hepatic metabolism. This modification protects the group from metabolic attack during the absorption process or first pass through the liver. However, the masking group must ultimately be removed to enable the drug to exert its maximum effect, and since the masking group is released into the body, it must be relatively non-toxic. This conversion may take place in blood or tissue. These types of masked drugs are usually referred to as prodrugs.

There are a number of examples in the literature which demonstrate the feasibility of the prodrug concept. However, it is apparent from these published studies that each drug class must be considered by itself. There is no way to accurately predict which prodrug structure will be suitable for a particular drug. A derivative which may work well for one drug may not do so for another. Differences in the absorption, metabolism, distribution, and excretion among drugs do not permit generalizations to be made about prodrug design.

Many of the above morphinans and partial morphinans are potent narcotic antagonists and/or analgesics which undergo extensive gastrointestinal and/or hepatic first-pass metabolism upon oral delivery, and thus have significantly decreased oral bioavailability. The need for strong analgesics with better oral bioavailability has long been recognized. None of the references cited, nor any known reference, suggest the novel morphinan N-oxides and partial morphinan N-oxides of the instant invention, or their desirability as prodrugs of morphinans and partial morphinans. Particularly unexpected is the fact that 3-hydroxy morphinans and partial morphinans exhibit significantly improved oral bioavailability when administered as the N-oxide derivatives.

SUMMARY OF THE INVENTION

In accordance with the present invention there are provided analgesic or narcotic antagonist pharmaceutical compositions formulated for oral administration, comprising a therapeutically effective amount of an N-oxide derivative of a 3-hydroxy morphinan or partial morphinan analgesic, agonist-antagonist, or narcotic antagonistic compound having improved oral bioavailability, and a pharmaceutically suitable carrier. Of particular interest are oral pharmaceutical compositions comprising an N-oxide derivative of 3-hydroxy morphinans or partial morphinans selected from the group consisting of the N-oxide of naloxone, naltrexone, nalbuphine, nalmefene, pentazocine, butorphanol, buprenorphine, oxymorphone, morphine, dihydromorphine, hydromorphone, levorphanol, levallorphan, and etorphine and pharmaceutically acceptable acid addition salts thereof, and a pharmaceutically suitable carrier. Preferred oral pharmaceutical compositions are those comprising the N-oxide of naloxone, naltrexone, nalbuphine, nalmefene, pentazocine, butorphanol, buprenorphine, or oxymorphone, and a pharmaceutically suitable carrier. More preferred oral pharmaceutical compositions are those comprising nalbuphine-N-oxide, naltrexone-N-oxide, or naloxone-N-oxide, and a pharmaceutically suitable carrier.

Reference to the 3-hydroxy morphinan and partial morphinan derivatives of this invention includes the pharmaceutically acceptable acid addition salts thereof. By the term "pharmaceutically acceptable acid addition salt" is meant any non-toxic pharmaceutically suitable salt of a compound described above which has the desired pharmacologic properties in mammals. Preparation of such salts is well known to those skilled in pharmaceutical science. Pharmaceutically acceptable acid addition salts of the above compounds include the hydrochloride, hydrobromide, hydroiodide, sulfate, bisulfate, nitrate, citrate, tartrate, bitartrate, lactate, phosphate, malate, maleate, fumarate, succinate, acetate and pamoate.

Also provided are derivatives of 3-hydroxy morphinan or partial morphinan analgesic, agonist-antagonist, or narcotic antagonist compounds, having improved oral bioavailability, selected from the group consisting of an N-oxide of naloxone, naltrexone, nalbuphine, nalmefene, pentazocine, butorphanol, buprenorphine, and oxymorphone.

Also provided are methods of treating pain, suppressing appetite, or reversing the effects of a narcotic drug such as morphine in a mammal which comprise administering orally to the mammal a therapeutically effective amount of an oral pharmaceutical composition as described above.

Specifically preferred for having improved oral bioavailability are nalbuphine N-oxide, naloxone N-oxide, and naltrexone N-oxide, pharmaceutical compositions thereof, and methods of treating pain or reversing the effects of narcotic analgesics using these drugs.

Also provided is a method for converting a 3-hydroxy morphinan or partial morphinan drug to its N-oxide prodrug, which comprises reacting the drug with a suitable oxidizing agent in a suitable solvent.

Although generally classified as either a narcotic analgesic, an agonist-antagonist, or a narcotic antagonist, the 3-hydroxy morphinan and partial morphinan compounds of this invention have other therapeutic utilities for which the orally effective dosage forms of the invention may be very useful. For example, morphine has useful sedative and antitussive properties as well as being a valuable analgesic. Hydromorphone is a useful antitussive as well as a potent analgesic. Certain narcotic antagonists and agonist-antagonists, for example naloxone, naltrexone, and nalmefene may be useful as appetite suppressants. Naloxone also has utility as an antidiarrheal, and for treatment of gastrointestinal disorders such as irritable bowel syndrome. Naloxone may be useful in treating male impotency, and since it lowers prolactin levels in males, it may also be beneficial in treating certain gynecological disorders, including infertility and menstrual and menopausal disorders. Naloxone has also been reported to reverse certain neurological deficits caused by anoxia, hemorrhage, aging (manifested by decreased cognition, alertness, etc.) and other pathological processes, and may speed healing once such processes have begun. Naloxone has also shown therapeutic activity in treating certain psychiatric disorders (hallucinations of schizophrenia) and chronic alcoholism. It also is said to exhibit antipruritic activity.

As used herein:

Naloxone means (−)-17-Allyl-4,5α-epoxy-3,14-dihydroxymorphinan-6-one, Formula (I), or a salt thereof.

Naltrexone means (−)-17-(Cyclopropylmethyl)-4,5α-epoxy-3,14-dihydroxymorphinan-6-one, Formula (II), or a salt thereof.

Nalbuphine means (−)-17-(Cyclobutylmethyl)-4,5α-epoxymorphinan-3,6α,14-triol, Formula (III), or a salt thereof.

Nalmefene means 6-Desoxo-6-methylene-naltrexone, Formula (IV), or a salt thereof.

Pentazocine means (−)-2-dimethallyl-5,9-dimethyl-2′-hydroxybenzomorphan, Formula (V), or a salt thereof.

Butorphanol means (−)-17-(Cyclobutylmethyl)-morphinan-3,14-diol, Formula (VI), or a salt thereof.

Buprenorphine means (−)-17-(Cyclopropylmethyl)-α-(1,1-dimethylethyl)-4,5-epoxy-18,19-dihydro-3-hydroxy-6-methoxy-α-methyl-6,14-ethenomorphinan-7-methanol, Formula (VII), or a salt thereof.

Oxymorphone means (−)-4,5α-Epoxy-3,14-dihydroxy-17-methylmorphinan-6-one, Formula (VIII), or a salt thereof.

Morphine means (−)7,8-Didehydro-4,5α-epoxy-17-methylmorphinan-3,6α-diol, or a salt thereof.

Hydromorphone means (−)4,5α-Epoxy-3-hydroxy-17-methylmorphinan-6-one, or a salt thereof.

Levorphanol means (−)-17-Methylmorphinan-3-ol, or a salt thereof.

Levallorphan means (−)-17 -Allyl-morphinan-3-ol, or a salt thereof.

Etorphine means (−)-4,5α-Epoxy-3-hydroxy-6-methoxy-α,17-dimethyl-α-propryl-6,14-ethenomorphinan-7α-methanol, or a salt thereof.

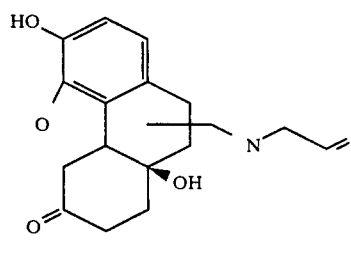

(I)

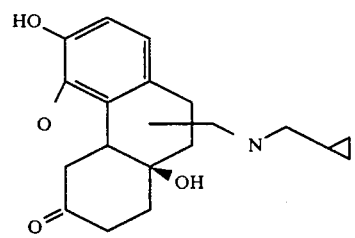

(II)

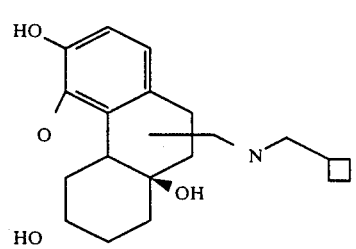

(III)

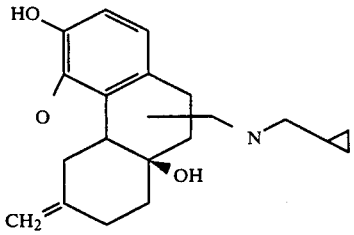

(IV)

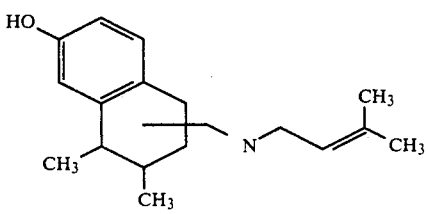

(V)

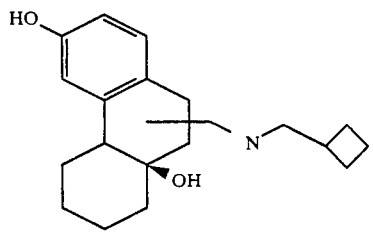

(VI)

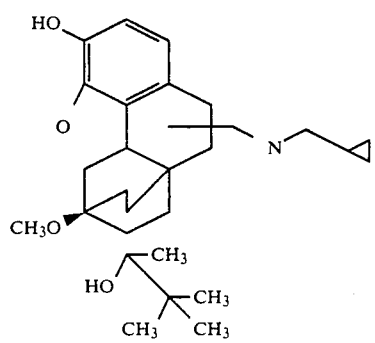

(VII)

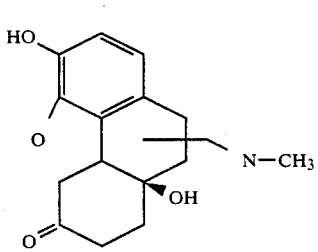

(VIII)

SYNTHESIS

There are a number of oxidizing agents that may be used to convert tertiary amines to tertiary amine N-oxides. Meta-chloroperbenzoic acid is convenient because it generally reacts rapidly to produce the N-oxide. However, other organic peracids may be used, such as performic acid, peracetic acid, perbenzoic acid, pertrifluoroacetic acid, permaleic acid, and perphthalic acid. Alternatively, the oxidizing agent may be produced in situ by dissolving the tertiary amine in an acid such as formic acid, acetic acid, or trifluoroacetic acid, and adding aqueous hydrogen peroxide of 3%–50% concentration, preferably of 30% to 50% concentration. An aprotic solvent such as methylene chloride, chloroform, or 1,2-dichloroethane, or a protic solvent such as methanol, ethanol, propanol, or tertiary butanol, may be used as the reaction medium, or if the oxidizing agent is generated in situ, the acid may optionally be used as the reaction medium.

Instead of using an organic peracid as described above, one may use a peroxide such as hydrogen peroxide. Aqueous hydrogen peroxide may be used alone in concentrations of 3% to 50%, or it may be used in a solvent such as those listed above. Other oxidizing agents which may be used include ozone, tertiary butyl hydroperoxide, and cumene hydroperoxide.

In general, the oxidizing agents are employed at temperatures between 0° C. and the boiling point of the solvent, more specifically between room temperature and the boiling point of the solvent, and for times between several minutes and three days, more specifically between one hour and 24 hours. The peroxide may be used in a ratio of one equivalent of peroxide to one equivalent of the amine, or an excess of peroxide may be used, such as between 10% and 100% excess or more. If, at the end of the reaction, excess peroxide is present (most easily detected with starch-iodide paper) it may be destroyed by adding an inorganic reducing agent such as sodium bisulfite or sodium sulfite, a metal catalyst such as 5% platinum or palladium on carbon or alumina, or an organic reducing agent such as dimethyl sulfide.

Other oxidizing agents that may be used for the preparation of tertiary amine oxides are ozone in a solvent such as chloroform, methylene chloride, a Freon, or methanol; ozone adsorbed on silica gel; and hydroperoxides such as tertiary butyl hydroperoxide, optional in the presence of a catalyst such as a vanadium compound.

When cost is important, for example in preparation on an industrial scale, the preferred reagent is 30%-50% aqueous hydrogen peroxide in tertiary butanol as solvent. For instance, several kilograms of nalbuphine may be oxidized to nalbuphine N-oxide, by reacting it with 50% aqueous hydrogen peroxide in boiling tertiary butanol for 2.5 hours.

Methods for preparation of a number of compounds of this invention are demonstrated in the following Examples. These same general methods may also be utilized for oxidation of other 3-hydroxy morphinans and partial morphinans to the corresponding N-oxides.

EXAMPLE 1

Nalbuphine N-oxide

Part A: Using m-Chloroperbenzoic Acid as Oxidant

A suspension of 10.7 g (0.03 mole) of nalbuphine in 300 mL of methylene chloride was treated with 6.7 g (0.039 mole) of powdered 85% m-chloroperbenzoic acid, added in portions over 15 minutes. After stirring at room temperature for one hour, no starting material was present by thin-layer chromatography. A test for peroxide with starch-iodide paper was negative. The solvent was removed by evaporation in vacuo, and the dry residue was dissolved in 300 mL of 2 M aqueous sodium bicarbonate solution. Crystallization was induced by scratching with a glass rod, and nalbuphine N-oxide hydrate was collected by filtration, washed with water and air dried. This material (weighing 11.0 g) was dissolved in 30 mL of methanol and the solution diluted with 30 mL of water. The product crystallized overnight and was collected by filtration, washed with cold methanol-water (1:5), and air-dried to provide 10.2 g of nalbuphine N-oxide, mp 175° C. (frothing). This product, which contained about 4% water, was stirred in 100 mL of ethyl acetate at reflux. The mixture was cooled to room temperature and filtered, and the solid washed with ethyl acetate and dried. The resulting material (9.9 g, 88%) contained about 1.4% water, and melted at 232-233° C. (Acetone may be substituted for ethyl acetate in the foregoing procedure). Product purity by analytical high pressure liquid chromatography was 99.7%.

NMR (DMSO-$d_6$, 200 mHz): $\delta$13.5 (s, 1H, 14-OH), 9.0 (s,1H, 3-OH), 6.5 (2d, 2H, 1-H and 2-H), 4.49 (d, 1H, 5$\beta$-H), and 4.40 (d, 1H, 6$\alpha$-OH), among others. Mass spectrum: m/z 373.1895 (calc. for $C_{21}H_{27}NO_5$–373.1889), 357.1909 (calc. for $C_{21}H_{27}NO_4$–357.1940). Chromatographic $R_f$: 0.14 (85:15 chloroform:ethanol, saturated with aqueous ammonium hydroxide).

Part B: Using Hydrogen Peroxide as Oxidant

Forty-three grams of nalbuphine were treated with 50% aqueous hydrogen peroxide in boiling t-butanol for 2.5 hours. After cooling to room temperature, the excess hydrogen peroxide was destroyed by adding an aqueous solution of sodium sulfite. The product precipitated as the hydrate, along with some sodium sulfate. This mixture was isolated by filtration, slurried with water to dissolve the sodium sulfate, filtered, and washed with water. The yield of crude nalbuphine N-oxide was 90-93%. Recrystallization from methanol-water provided the title product of 99.7% purity, in 85% yield.

EXAMPLE 2

Naltrexone N-oxide

Naltrexone [2.05 g (6 mmole)] and 1.35 g (7.8 mmole) of 85% m-chloroperbenzoic acid were added to 60 mL of methylene chloride, and the mixture was heated at reflux overnight. No peroxide was present (by starch-iodide paper). The solvent was evaporated and the residue was dissolved in 2 M aqueous sodium bicarbonate. The product was isolated by extraction with 3 × 50 mL of chloroform, dried with sodium sulfate, filtered, and concentrated. This material was chromatographed on silica gel (92:8 chloroform:methanol) to give 1.27 g (60.5%) of naltrexone N-oxide, mp 260° C.

NMR (DMSO-$d_6$, 200 mHz): $\delta$13.25 (s, 1H, 14-OH), 9.4 (s, 1H, 3-OH), 6.6 (q, 2H, 1-H and 2-H), and 4.85 (s, 1H, 5$\beta$-H), among others.

EXAMPLE 3

Following the procedure of Example 2, 8.18 g (25 mmole) of naloxone and 4.31 g (25 mmole) of 99+% m-chloroperbenzoic acid in 250 mL of methylene chloride provided 6.43 g of crude naloxone N-oxide. This material was stirred in boiling methanol, isolated by filtration, then stirred in boiling chloroform, isolated by filtration, and recrystallized from methanol-chloroform to provide 1.96 g (70%) of naloxone N-oxide, mp 189-190° C.

NMR (DMSO-$d_6$, 200 mHz): $\delta$12.5 (s, 1H, 14-OH), 9.25 (s, 1H, 3-OH), 6.5 ($A_2B_2$ pattern, 2H, 1-H and 2-H), 5.8 m, 1H, -CH=C), 5.2 (m, 2H, C=$CH_2$), and 4.7 (s, 1H, 5$\beta$-H), among others.

Mass spectrum: m/z 343.1416 (calc. for $C_{19}H_{21}NO_5$—343.1419), 327.1475 (calc. for $C_{19}H_{21}NO_4$—327.1471).

EXAMPLE 4

Oxymorphone N-oxide

Oxymorphone [1.05 g (3.5 mmole)] was suspended in 30 mL of methylene chloride and heated to reflux. 780 mg (4.6 mmole) of 85% m-chloroperbenzoic acid was added in three equal portions over 30 minutes. All of the solids dissolved after the last addition. After 5 minutes more, a precipitate appeared. A test for peroxides with starch-iodide paper was negative. The solvent was evaporated, the residue was dissolved in 2 M aqueous sodium bicarbonate, and this solution was extracted with 3×25 mL of chloroform. The organic phase was dried with sodium sulfate, filtered and evaporated. The resulting material was triturated with methanol, isolated by filtration, washed with a small amount of methanol, and recrystallized from methanol to provide 830 mg (75%) of oxymorphone N-oxide, mp 253-255° C.

NMR (DMSO-d$_6$, 200 mHz): δ12.95 (s, 1H, 14-OH), 9.45 (s, 1H, 3-OH), 6.65 (A$_2$B$_2$ pattern, 2H, 1-H and 2-H), 4.9 (s, 1H, 5β-H), and 3.2 (s, 3H, N-CH$_3$), among others.

Mass spectrum: m/z 317.1235 (calc. for $C_{17}H_{19}NO_5$—317.1263), 301.1298 calc. for $C_{17}H_{19}NO_4$—301.1314).

Chromatographic R$_f$: 0.24 (85:15 chloroform:ethanol),

EXAMPLE 5

Butorphanol N-oxide

Butorphanol [1.16 g (3.5 mmole)] and 30 mL of methylene chloride were combined and stirred, and 0.79 g (4.6 mmole) of 85% m-chloroperbenzoic acid was added. After one hour, the solvent was evaporated and the residue was slurried with 2 M aqueous sodium bicarbonate. The precipitate was isolated by filtration, washed with water, and air-dried. The crude product was chromatographed on silica gel (95:5 chloroform-methanol) to give 750 mg (62.5%) of butorphanol N-oxide, mp 167° C. (frothing).

NMR (DMSO-d$_6$, 200 mHz): δ11.65 (s, 1H, 14-OH), 9.25 (s, 1H, 3-OH), 6.95 (d, 1H, 1-H), 6.65 (s showing meta coupling, 1H, 4-H), and 6.55 (d showing meta coupling, 1H, 2-H), among others.

The compounds of Examples 1-5, and certain other N-oxides of 3-hydroxy morphinans and partial morphinans which were prepared or can be prepared using the procedures of Examples 1-5, are shown in Table I.

TABLE I

| Example | Compound | Yield | Melting Point (° C.) |
|---|---|---|---|
| 1a | Nalbuphine N-oxide | 88% | 232-233 |
| 1b | Nalbuphine N-oxide | 85% | 232-233 |
| 2 | Naltrexone N-oxide | 60.5% | 260 |
| 3 | Naloxone N-oxide | 70% | 189-190 |
| 4 | Oxymorphone N-oxide | 75% | 253-255 |
| 5 | Butorphanol N-oxide | 62.5% | 167 |
| 6 | Nalmefene N-oxide | 52% | 243-4 |
| 7 | Pentazocine N-oxide | | |
| 8 | Buprenorphine N-oxide | | |
| 9 | Morphine N-oxide | 50% | 274-5 |
| 10 | Hydromorphone N-oxide | | |
| 11 | Levorphanol N-oxide | | |
| 12 | Levallorphan N-oxide | | |
| 13 | EtorPhine N-oxide | | |

Dosage Forms

The N-oxide prodrugs of the instant invention can be administered orally to treat pain, to reverse the effects of narcotic drugs, or to achieve the other therapeutic effects discussed above using any oral formulation that results in the active agent reaching the agent's site of action in the body of a mammal. They can be administered by any of the various means known to be suitable for pharmaceuticals, either as individual analgesic agents or a combination of therapeutic agents. Although these drugs can be administered alone, they are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of recipient; nature and extent of symptoms, kind of concurrent treatment, frequency of treatment, and the effect desired. Usually a daily dosage of prodrug can be about 0.1 to 50 milligrams per kilogram of body weight. Ordinarily, when the more potent compounds of this invention are used, 0.1 to 20 milligrams per kilogram per day, given in divided doses 2 to 4 times a day or in sustained release form, is effective to obtain desired results.

Dosage forms (compositions) suitable for internal administration contain from about 0.5 to 500 milligrams of prodrug per unit. In these pharmaceutical compositions the N-oxide prodrug will ordinarily be present in an amount of about 0.5 to 95% by weight based on the total weight of the composition.

The N-oxide prodrugs of the instant invention can be administered orally in solid dosage forms, such as capsules, tablets, and powders, or in liquid dosage forms, such as elixirs, syrups, and suspensions.

Hard gelatin capsules contain the N-oxide prodrug and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered prodrug, 150 milligrams of lactose, 1.5 milligrams of colloidal silicon dioxide, 3 milligrams of magnesium stearate and 70.5 milligrams of a cellulose derivative.

Soft Gelatin Capsules

A mixture of a prodrug in an edible vegetable oil, polyethylene glycol, or any other suitable carrier is prepared and injected by means of a positive displacement pump into gelatin to form soft gelatin capsules each containing 75 milligrams of the prodrug. The capsules are washed in petroleum ether and dried.

Tablets

A large number of tablets are prepared by conventional procedures so that the dosage unit is 75 milligrams of the prodrug, 1.5 milligrams of colloidal silicon dioxide, 5.5 milligrams of magnesium stearate, 83 milligrams of microcrystalline cellulose, 15 milligrams of starch and 120 milligrams of lactose. Appropriate coatings may be applied to increase palatability or delay absorption.

Suspension

An aqueous suspension is prepared for oral administration so that each 5 milliliters contain 75 milligrams of finely divided prodrug, 200 milligrams of sodium carboxymethyl cellulose, 5 milligrams of sodium benzoate, 1.0 grams of sorbitol solution, U.S.P., and 0.025 milliliters of vanillin.

UTILITY

Test results indicate that the compounds of this invention are useful in providing enhanced bioavailability of 3-hydroxy morphinan and partial morphinan analgesics, mixed agonist-antagonists, and narcotic antagonists from orally administered dosage forms. The N-oxides have a relatively low affinity for opiate receptors and would not be expected to have significant pharmacologic activity unless reduced to the parent compounds.

METHODS

Among the experiments used to evaluate the N-oxide prodrugs of the instant invention were measurements of their reduction rates in vitro by various biological media from rats, dogs, and humans, and drug bioavailability in rats and dogs administered oral doses of the prodrug. Drug concentration was determined after solvent extraction, using high pressure liquid chromatography analytical procedures.

IN VITRO REDUCTION

Prodrug was added to fresh biological medium to a concentration of 0.28 μM, incubated at 37° C., and the rate of drug appearance was measured.

ORAL DRUG BIOAVAILABILITY

Rats and dogs were administered the parent drug intravenously and orally, and the prodrugs were administered orally. Usually, doses were administered as aqueous solutions prepared immediately before dosing. Plasma was collected and frozen until analysis of drug concentration. The area under the plasma drug concentration versus time curve (AUC) was calculated for each animal. Bioavailability (F) was estimated by:

$$F = \frac{AUC(po) \times Dose(iv)}{AUC(iv) \times Dose(po)} \times 100\%$$

F represents the percentage of the administered dose absorbed into plasma. Relative bioavailability (RB) of parent drug was determined by comparing the bioavailability from orally administered prodrug F(pro) with the bioavailability from orally administered parent drug F(drug).

$$RB = \frac{F(pro)}{F(drug)}$$

NALBUPHINE RESULTS

Table II shows the percent bioavailability of oral nalbuphine in a variety of species. In terms of oral bioavailability of nalbuphine, the dog (5.4%) most closely resembles the human (14%) of those species examined.

TABLE II

| ORAL NALBUPHINE BIOAVAILABILITY (% DOSE; MEAN ± SE) | |
|---|---|
| Rat | 2.7 ± 0.4 (a) |
| Dog | 5.4 ± 0.9 (b) |
| Monkey | 0.9 ± 1.6 (b) |
| Human | 14 (c) |

(a) 20 mg Nalbuphine /kg
(b) 4 mg Nalbuphin /kg
(c) 45 mg tablet or solution

Table (III) shows the reduction rate of Nalbuphine N-oxide in a variety of biological media.

TABLE III

| RATES OF CONVERSION OF NALBUPHINE N-OXIDE TO NALBUPHINE IN VARIOUS BIOLOGICAL MEDIA AT 37° C. IN VITRO | |
|---|---|
| MEDIUM | RATE |
| Human Plasma | negligible |
| Dog Plasma | $t_{\frac{1}{2}}$=53.7 hours |
| Rat Plasma | $t_{\frac{1}{2}}$=6.0 hours |
| Rat liver homogenate (25%) | 100% in 3 minutes |
| Rat intestine homogenate (25%) | 100% in 10 minutes |

Table IV shows the relative bioavailability of nalbuphine in dogs and rats from orally administered doses of nalbuphine and nalbuphine N-oxide.

TABLE IV

| NALBUPHINE BIOAVAILABILITY IN DOGS AND RATS | | | |
|---|---|---|---|
| SPECIES | F(DRUG) | F(PRO) | RB |
| Dog | 5.4 ± 0.9 | 53.5 ± 8.4 | 9.9 |
| Rat | 2.7 ± 0.4 | 14.2 ± 2.5 | 5.3 |

NALTREXONE RESULTS

The effectiveness of naltrexone-N-oxide in increasing oral naltrexone bioavailability if demonstrated in the relative plasma naltrexone concentration versus the profiles given in Table V.

TABLE V

Average Plasma Naltrexone Concentrations Normalized for Dose in Separate Groups of Dogs Administered Oral Doses of (A) Naltrexone or (B) Naltrexone-N-Oxide

| Hours | Plasma Naltrexone Conc. (ng/ml) | |
|---|---|---|
| | A | B |
| 0.25 | 9 | 424 |
| 0.5 | 9 | 752 |
| 1 | 4 | 713 |
| 1.5 | 4 | 559 |
| 2 | 0 | 484 |
| 3 | 0 | 251 |
| 4 | 0 | 110 |
| 6 | 0 | 24 |
| 8 | 0 | 8 |

Naloxone Results

Oral naloxone bioavailability was improved when administered as the N-oxide, relative to naloxone, as shown by the plasma naloxone concentration in Table VI.

TABLE VI

Average Plasma Naloxone Concentrations Vs. Time in Separate Groups of Dogs Administered Equimolar Oral Doses of (A) Naloxone or (B) Naloxone-N-Oxide

| Hours | Plasma Naloxone Conc. (ng/ml) | |
|---|---|---|
| | A | B |
| 0.5 | 451 | 947 |
| 1 | 176 | 1223 |
| 2 | 65 | 797 |
| 3 | 30 | 289 |
| 4 | 10 | 107 |
| 6 | 10 | 22 |
| 8 | 5 | 6 |

We claim:

1. A compound selected from the group consisting of an N-oxide derivative of naloxone, naltrexone, nalbuphine, nalmefene, pentazocine, butorphanol, and buprenorphine.

2. A compound of claim 1 which is nalbuphine-N-oxide, naltrexone-N-oxide, or naloxone-N-oxide.

* * * * *